US00PP10304P

United States Patent [19]

Kientzler

[11] Patent Number: Plant 10,304

[45] Date of Patent: Mar. 24, 1998

[54] NEW GUINEA IMPATIENS PLANT NAMED 'TOGA'

[75] Inventor: Ludwig Kientzler, Gensingen, Germany

[73] Assignee: Paul Ecke Ranch, Inc., Encinitas, Calif.

[21] Appl. No.: 778,904

[22] Filed: Jan. 3, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea Impatiens plant named 'Toga', characterized by its flat and rounded lavender-colored flowers; upright to outwardly spreading, rounded and mounding growth habit; and dark green, somewhat glossy, non-variegated foliage.

1 Drawing Sheet

1

The present invention relates to a new and distinct cultivar of New Guinea Impatiens plant, botanically known as *Impatiens hawkeri*, known by the name 'Kitoga', and hereinafter referred to by the cultivar name 'Toga'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as L926 as the male, or pollen parent, with the proprietary seedling selection identified as W525 as the female, or seed patent. The cultivar 'Toga' was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Toga'. These characteristics in combination distinguish 'Toga' as a new and distinct cultivar:

1. Flat and rounded lavender-colored flowers.
2. Upright to outwardly spreading, rounded and mounding growth habit.
3. Dark green, somewhat glossy, non-variegated foliage.

The new New Guinea Impatiens is similar in flower color to the New Guinea Impatiens cultivar 'Light Lavender II' (disclosed in U.S. Plant Pat. No. 9,278). However in side-by-side comparisons in Encinitas, Calif., under commercial practice, plants of the new New Guinea Impatiens differed from plants of the cultivar 'Light Lavender II' in the following characteristics:

1. Plants of the new New Guinea Impatiens are more outwardly spreading and mounding than plants of the cultivar 'Light Lavender II'.
2. Plants of the new New Guinea Impatiens less vigorous than plants of the cultivar 'Light Lavender II'.
3. Plants of the new New Guinea Impatiens are more freely branching than plants of the cultivar 'Light Lavender II'.
4. Leaves of plants of the new New Guinea Impatiens are shorter than leaves of plants of the cultivar 'Light Lavender II'.
5. Flowers of plants of the new New Guinea Impatiens are more rounded and flatter than flowers of plants of the cultivar 'Light Lavender II'.

2

6. Flower spurs of plants of the new New Guinea Impatiens are shorter and more red than flower spurs of plants of the cultivar 'Light Lavender II'.
7. Peduncles of plants of the new New Guinea Impatiens are shorter, stronger and more red than flower spurs of plants of the cultivar 'Light Lavender II'.

A detailed comparison of plants of the new New Guinea Impatiens and the cultivar 'Light Lavender II' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Toga'.

The second photograph comprises a close-up view of typical flowers and upper (left) and lower (right) surfaces of leaves of the cultivars 'Light Lavender II' (top of photo) and 'Toga' (bottom of photo).

Flower and foliage colors in the photographs may differ from the actual colors due to light reflectance.

The cultivar Toga has not been observed under all possible environmental conditions. The phenotype may vary somewhat with variations inenvironment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C and night temperatures ranging from 16 to 18C and light levels averaging 3,000 footcandles.

In the following description, color references are made to The Royal Horticultural Society Colour Chart except where general terms of ordinary dictionary significance are used.

Classification:

*Botanical.*—*Impatiens hawkeri* 'Toga'.

*Commercial.*—New Guinea Impatiens cv. 'Toga'.

Parentage:

*Male parent.*—Proprietary seedling selection L926.

*Female parent.*—Proprietary seedling selection W525.

Propagation:

*Type cutting.*—Terminal cuttings.

*Time to initiate roots.*—about 15 days with 21C soil temperature.

Plant Description:

*Plant form.*—Upright to outwardly spreading, mounded and compact.

*Growth habit.*—Moderately vigorous. Moderate branching, dense and bushy. Suitable for 10 to 25-cm containers.

*Plant size.*—Height: About 18 cm. Width or spread: About 21 cm.

*Lateral branches.*—Quantity: Five to seven. Size: Length: About 14 cm. Diameter: 1 to 1.3 cm. Internode length: 4 to 5 cm. Color: 146A with thin stripes of 59A.

*Foliage description.*—Leaves simple, generally symmetrical, abundant, opposite or in whorls of three, horizontal to plant and flat in aspect. Size, largest leaves: Length: About 11.5 cm. Width: About 4.5 cm. Shape: Ovate with acuminate apex, attenuate base and ciliate margin. Texture: Smooth, somewhat glossy. Color: Young foliage, upper surface: 137A. Young foliage, lower surface: 147B. Fully expanded foliage, upper surface: 147A. Fully expanded foliage, lower surface: 147B. Venation, upper surface: 147B. Venation, lower surface: Moderately deep reddish brown. Petiole: Size: Length: About 3.5 cm. Diameter: About 3 mm. Color: 182A.

Flower description:

*Flower type and habit.*—Lavender-colored flowers. Freely and continuously flowering. Flowers arise from leaf axils. Usually eight flowers per lateral branch. Flowers positioned at or just above the foliage and face upward or outward. Flowers flat and rounded. Flowers persistent.

*Flowering season.*—Year-round under greenhouse conditions. In the garden, flowering is continuous from spring until fall.

*Flower size.*—Length: About 6 cm. Width: About 6 cm. Depth: About 5 mm.

*Flower buds.*—Size: Length: About 2.3 cm. Diameter: About 1.6 cm. Shape: Ovoid. Color: 72B.

*Petals.*—Quantity: Five. Size (largest petals): Length: Top petal: About 2.6 cm. Middle petals: About 2.8 cm. Bottom petals: About 3.5 cm. Width: Top petal: About 4 cm. Middle petals: About 2.6 cm. Bottom petals: About 3.6 cm. Shape: Cordate with emarginate apex, cuneate or obtuse base and entire margin. Texture: Velvety, smooth. Color: When opening, upper surface: Iridescent, 81C. When opening, lower surface: Iridescent, 81D. Fully opened, upper surface: Iridescent, 82C. Fully opened, lower surface: Iridescent, 82D Fading to: Slightly lighter than 82D.

*Spur.*—length: About 4.5 cm. Shape: Narrow and curved. Color: Proximal: 148C with 59C overtones. Distal: 59A.

*Peduncles.*—Length: About 4 cm. Angle: Erect and outward. Strength: Strong. Color: 59A.

*Reproductive organs.*—Androecium: Stamen number: Five, anthers fused, filaments free. Anther shape: Obovate. Anther size: 5 by 4 mm. Anther color: Cream. Amount of pollen: Moderate. Pollen color: Cream. Gynoecium: Five-loculate fused. Gynoecium color: 58B.

Disease Resistance: Under commercial conditions, resistance nor susceptibility to pathogens has not been observed.

Seed development: Seed production is not usually observed.

CHART A

| CHARACTERISTIC | 'TOGA' | 'LIGHT LAVENDER II' |
|---|---|---|
| GROWTH HABIT | Upright to outwardly spreading and mounding | Upright, open |
| VIGOR | Moderate | Vigorous |
| NUMBER OF LATERAL BRANCHES | 5 to 7 | 3 to 5 |
| LATERAL BRANCH LENGTH | About 14 cm | About 17 cm |
| LATERAL BRANCH DIAMETER | 1 to 1.3 cm | 0.8 to 1 cm |
| LEAF LENGTH | About 11.5 cm | About 13 cm |
| LEAF WIDTH | About 4.5 cm | 4.5 to 5 cm |
| LEAF COLOR, YOUNG, UPPER SURFACE | 137A | 137A |
| LEAF COLOR, YOUNG, LOWER SURFACE | 147B | 147C |
| LEAF COLOR, MATURE, UPPER SURFACE | 147A | 147A |
| LEAF COLOR, MATURE, LOWER SURFACE | 147B | 147C |
| LEAF VENATION COLOR, UPPER SURFACE | 147B | Lighter than 146D |
| LEAF VENATION COLOR, LOWER SURFACE | 148A | 146D |
| PETIOLE LENGTH | About 3.5 cm | About 4 cm |
| PETIOLE DIAMETER | About 3 mm | About 5 mm |
| PETIOLE COLOR | 182A | 184D |
| FLOWER ASPECT | Flat | Slightly cupped |
| FLOWER SHAPE | Rounded | Slightly cupped |
| FLOWER LENGTH | About 6 cm | About 6 cm |
| FLOWER WIDTH | About 6 cm | About 5 cm |
| PETAL COLOR, WHEN OPENING, UPPER SURFACE | 81C | 81C |
| PETAL COLOR, WHEN OPENING, LOWER SURFACE | 81D | 82D |
| PETAL COLOR, OPENED, UPPER SURFACE | 82C | 81D |
| PETAL COLOR, OPENED, LOWER SURFACE | 82D | 75C |
| PETAL COLOR FADING TO | Slightly lighter than 82D | 75B |
| SPUR LENGTH | About 4.5 cm | About 6 cm |
| SPUR COLOR | Proximal: 148C with 59C overtones Distal: 59A | Proximal: Lighter than 145D Distal: 145C with 182B tip |
| PEDUNCLE LENGTH | About 4 cm | 4.5 to 5 cm |
| PEDUNCLE STRENGTH | Strong | Moderate to strong |
| PEDUNCLE COLOR | 59A | 144B |
| FLOWER BUD COLOR | 72B | 82D |

It is claimed:

1. A new and distinct cultivar of New Guinea Impatiens plant named 'Toga', as illustrated and described.

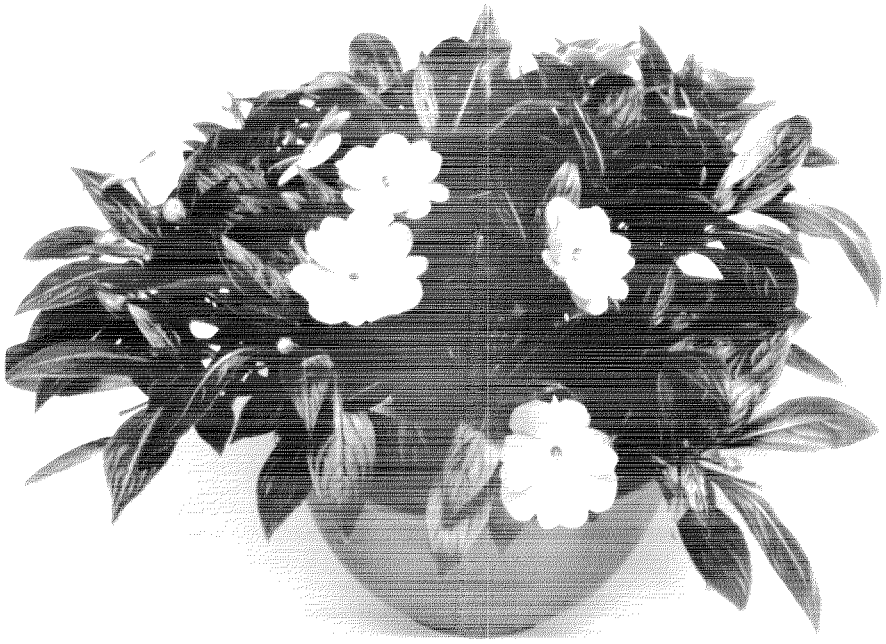
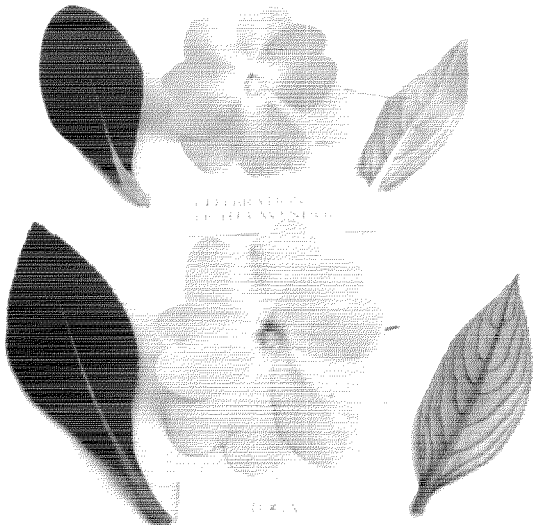

* * * * *